United States Patent
Raak et al.

(10) Patent No.: US 11,532,009 B1
(45) Date of Patent: Dec. 20, 2022

(54) FOOD PORTIONING SYSTEM AND RELATED METHODS

(71) Applicant: Inmar Clearing, Inc., Winston-Salem, NC (US)

(72) Inventors: Alise Raak, Winston-Salem, NC (US); Diana Medina, Winston-Salem, NC (US)

(73) Assignee: INMAR CLEARING, INC., Winston-Salem, NC (US)

( * ) Notice: Subject to any disclaimer, the term of this patent is extended or adjusted under 35 U.S.C. 154(b) by 299 days.

(21) Appl. No.: 16/799,459

(22) Filed: Feb. 24, 2020

(51) Int. Cl.
| | |
|---|---|
| *G06Q 30/02* | (2012.01) |
| *G16H 10/60* | (2018.01) |
| *G16H 20/60* | (2018.01) |
| *G01G 19/414* | (2006.01) |
| *G01G 23/18* | (2006.01) |
| *A61B 5/00* | (2006.01) |
| *G06Q 30/06* | (2012.01) |
| *H04W 4/20* | (2018.01) |

(52) U.S. Cl.
CPC ....... *G06Q 30/0224* (2013.01); *A61B 5/4866* (2013.01); *G01G 19/4146* (2013.01); *G01G 23/18* (2013.01); *G06Q 30/0631* (2013.01); *G16H 10/60* (2018.01); *G16H 20/60* (2018.01); *H04W 4/20* (2013.01)

(58) Field of Classification Search
CPC ........... G06Q 30/0224; G06Q 30/0631; G01G 19/4146; G01G 23/18; G16H 20/60
See application file for complete search history.

(56) References Cited

U.S. PATENT DOCUMENTS

| | | |
|---|---|---|
| 9,442,100 B2 | 9/2016 | Connor |
| 2014/0186805 A1 | 7/2014 | Pordy |

(Continued)

OTHER PUBLICATIONS

"Fitly's SmartPlate takes cognitive to heart with Watson IoT" (Lewis, Karen published at https://www.ibm.com/blogs/internet-of-things/cognitive-smartplate/on Mar. 20, 2017) (Year: 2017).*

(Continued)

*Primary Examiner* — James M Detweiler
(74) *Attorney, Agent, or Firm* — Allen, Dyer, Doppelt + Gilchrist, P.A.

(57) ABSTRACT

A food portioning system may include a food plate body and a scale associated with the food plate body to sense a weight of food carried thereby. The system may also include wireless communications circuitry coupled to the scale, and a mobile wireless communications device associated with a given user. The mobile wireless communications device may be configured to obtain a user-selected food recipe from the given user, obtain user health data associated with the given user, and obtain a desired consumable food weight for the food plate body based upon the user-selected food recipe and the user health data associated with the given user. The mobile wireless communications device may also be configured to wirelessly communicate with the wireless communications circuitry to obtain a sensed consumable food weight, compare the sensed consumable food weight with the desired consumable food weight, and generate a notification based upon the comparing.

10 Claims, 5 Drawing Sheets

(56) References Cited

U.S. PATENT DOCUMENTS

| | | | | |
|---|---|---|---|---|
| 2016/0078467 | A1* | 3/2016 | Vosters | G06Q 30/02 |
| | | | | 705/14.33 |
| 2016/0125446 | A1* | 5/2016 | Gonen | G06Q 30/0631 |
| | | | | 705/14.27 |
| 2016/0260352 | A1* | 9/2016 | Ortiz | G09B 19/00 |
| 2017/0116391 | A1* | 4/2017 | Yoon | G16H 10/60 |
| 2018/0233064 | A1* | 8/2018 | Dunn | G09B 19/0092 |
| 2019/0080629 | A1* | 3/2019 | Gopalan | G06V 20/20 |
| 2019/0099124 | A1* | 4/2019 | Mattis | A61B 5/0022 |
| 2021/0134434 | A1* | 5/2021 | Riley | G16H 50/30 |
| 2021/0186241 | A1* | 6/2021 | Kramer | A47G 19/025 |

OTHER PUBLICATIONS

SmartPlate; "Your Personal Nurtitionist;" https://www.getsmartplate.com/; 6 pages; 2018.
INDIEGOGO; "Smart Plate Top View: Your Personal Nutritionist;" https://www.indiegogo.com/projects/smart-plate-topview-your-personal-nutritionist#/; 19 pages; 2017.

* cited by examiner

FOOD PORTIONING SYSTEM AND RELATED METHODS

TECHNICAL FIELD

The present invention relates to the field of food, and more particularly, to food portioning systems and related methods.

BACKGROUND

Overeating may be considered a factor for increased weight gain and, thus decreased health. Accordingly, it may be desirable to manage food intake during any given meal, for example, managing caloric intake. One way of managing caloric intake is to manually weigh each food item to be consumed and calculate the total calories for each food item.

A food recipe typically includes a set of instructions that describes how to prepare or make a meal or prepared food. Recipes were typically printed in books or other print media. With the increasing popularity of electronic commerce (e-commerce), an increasing amount of recipes are being published online.

Sales of a particular product or service may be based upon how well that product or service is marketed to a consumer. One form of marketing is a coupon, typically in paper form, for a discount toward the product or service. Some coupons may be retailer-specific, for example, only redeemable for the discount at a particular retailer, while other coupons may be product-specific from a manufacturer and redeemable at any retailer.

A coupon, while typically in paper form, may be in digital form and may be referred to as a digital promotion. A digital promotion may be selected or "clipped" via a mobile phone and saved to a digital wallet for redemption at a point-of-sale (POS) terminal, for example. A typical coupon is applicable to a given product and has a redeemable value that may vary based upon the quantity of a given item, for example, brand of item, size of the product in terms of packaging, and/or the price point of the given item. A typical coupon may also be redeemable only at a given retailer and/or within a threshold time period.

U.S. Patent Application Publication No. 2014/0186805 to Pordy is directed to a portion control aid and method of making and using the same includes a transparent base with portion-indicating markings. The portion indicating-markings form portion-indicating regions. The size of the portion indicating regions correspond with the size of a perimeter of a portion of food that is equal to a desired or recommended portion. When the food consists of pieces that can be formed in a pile or scoop, the markings are determined by the expected Angle of Repose of the pile or scoop. In use the transparent base is held directly above the portion of food with the portion indicating region generally aligned with the portion of food. If the entire portion of food visually appears to fit within the portion-indicating region, the portion of food contains no more than the desired or recommended portion.

SUMMARY

A food portioning system may include a food plate body, and at least one scale associated with the food plate body and configured to sense a weight of food carried thereby. The food portioning system may also include wireless communications circuitry coupled to the at least one scale, and a mobile wireless communications device associated with a given user. The mobile wireless communications device may be configured to obtain a user-selected food recipe from the given user, obtain user health data associated with the given user, and obtain a desired consumable food weight for the food plate body based upon the user-selected food recipe and the user health data associated with the given user. The mobile wireless communications device may also be configured to wirelessly communicate with the wireless communications circuitry to obtain a sensed consumable food weight, and compare the sensed consumable food weight with the desired consumable food weight, and generate a notification based upon the comparing.

The food portioning system may further include a promotional server configured to obtain the user-selected food recipe from the mobile wireless communications device, generate a digital promotion based upon the user-selected food recipe, and communicate the digital promotion to the mobile wireless communications device. The digital promotion may be for another food recipe having at least one common ingredient with the user-selected food recipe, for example.

The digital promotion may be for another food recipe having a higher nutritional value than the user-selected food recipe. The promotional server may be configured to set a promotional value of the digital promotion based upon the user health data, for example.

The mobile wireless communications device may be configured to obtain a nutritional value for the user-selected food recipe, and determine the desired consumable food weight based upon the nutritional value. The user health data may include at least one of user weight data, user age data, user gender data, user fitness data, user nutritional goal data, and user biometric data, for example.

The food plate body may include at least one partition defining a plurality of food compartments, and the at least one scale may include a plurality of scales each corresponding to a respective food compartment. The at least one scale may be coupled to the food plate body. The at least one scale may be configured to carry the food plate body, for example.

A method aspect is directed to a method of portioning food in a food portioning system that includes a food plate body, at least one scale associated with the food plate body and configured to sense a weight of food carried thereby, and wireless communications circuitry coupled to the at least one scale. The method may include using a mobile wireless communications device to obtain a user-selected food recipe from the given user, obtain user health data associated with the given user, and obtain a desired consumable food weight for the food plate body based upon the user-selected food recipe and the user health data associated with the given user. The mobile wireless communications device may also be used to wirelessly communicate with the wireless communications circuitry to obtain a sensed consumable food weight, and compare the sensed consumable food weight with the desired consumable food weight, and generate a notification based upon the comparing.

A computer readable medium aspect is directed to a non-transitory computer readable medium for portioning food in a food portioning system. The food partitioning system may include a food plate body, at least one scale associated with the food plate body and configured to sense a weight of food carried thereby, and wireless communications circuitry coupled to the at least one scale. The non-transitory computer readable medium may include computer executable instructions that when executed by a processor cause the processor to perform operations. The operations may include obtaining a user-selected food recipe from the given user, obtaining user health data associated with the given user, and obtaining a desired consumable food weight for the food plate body based upon the user-selected food recipe and the user health data associated with the given user. The operations may also include wirelessly communicating with the wireless communications circuitry to obtain a sensed consumable food weight, and comparing the sensed consumable food weight with the desired consumable food weight, and generating a notification based upon the comparing.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation is used to indicate similar elements in alternative embodiments.

Figure 1:
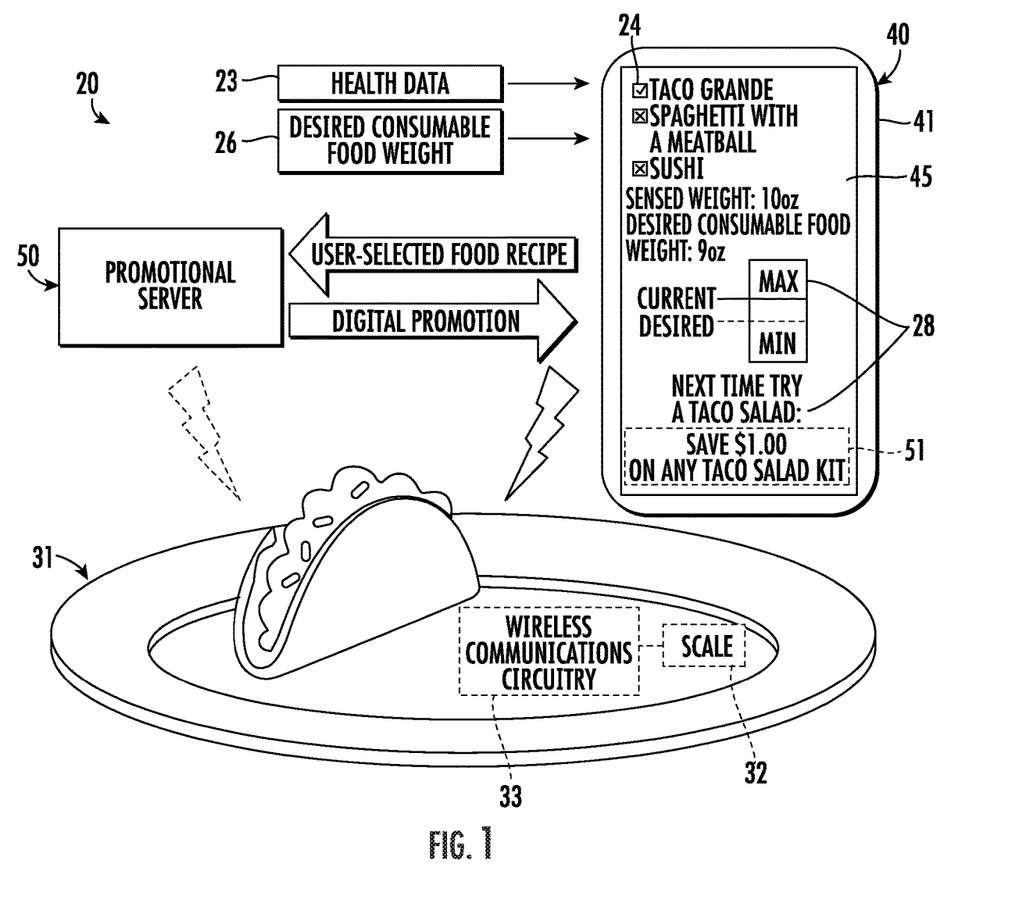
FIG. 1 is a schematic diagram of a food portioning system in accordance with an embodiment.
Figure 2:
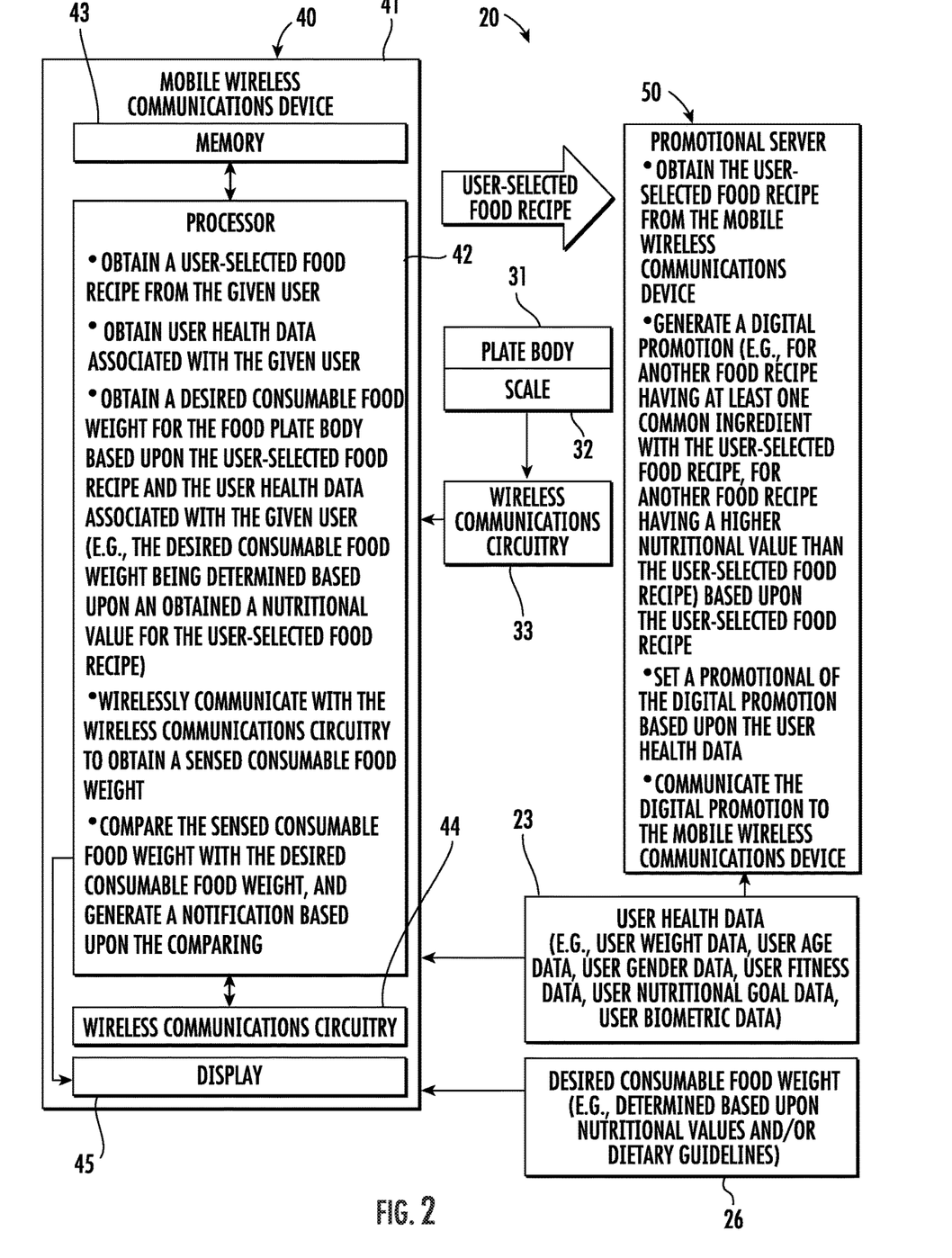
FIG. 2 is a schematic block diagram of the food portioning system of FIG. 1.

Referring initially to FIGS. 1-2 a food portioning system 20 includes a food plate body 31. While illustratively in the form of a plate with a relatively small sidewall, the food plate body 31 may have one or more sidewalls that are relatively high to define a bowl.

A scale 32 is associated with the food plate body 31. More particularly, the food plate body 31 defines a housing, and the scale 32 is carried within the housing. The scale 32 senses a weight of food carried thereby.

Wireless communications circuitry 33 is coupled to the scale 32. The wireless communications circuitry 33, similarly to the scale 32, may be carried within the housing defined by the food plate body 31. The wireless communications circuitry 33 may include WiFi communications circuitry, cellular communications circuitry, Bluetooth™ wireless communications circuitry, near-field communications (NFC) wireless communications circuitry, and/or other types of long or short-range wireless communications circuitry as will be appreciated by those skilled in the art.

The food portioning system 20 also includes a mobile wireless communications device 40 associated with a given user. The mobile wireless communications device 40 illustratively includes a portable housing 41, a mobile processor 42 or controller, memory 43 coupled to the mobile processor, and mobile device wireless communications circuitry 44 coupled to the mobile processor. The mobile wireless communications device 40 also includes a display 45, such as, for example, a touch display, carried by the portable housing 41 and coupled to the mobile processor 42. The mobile wireless communications device 40 may include one or more input devices, for example, a camera and other types of input or output devices. The mobile wireless communications device 40, while illustratively a mobile phone or smartphone, may be a tablet computer, or other type of mobile wireless communications device, as will be appreciated by those skilled in the art.

Figure 3:
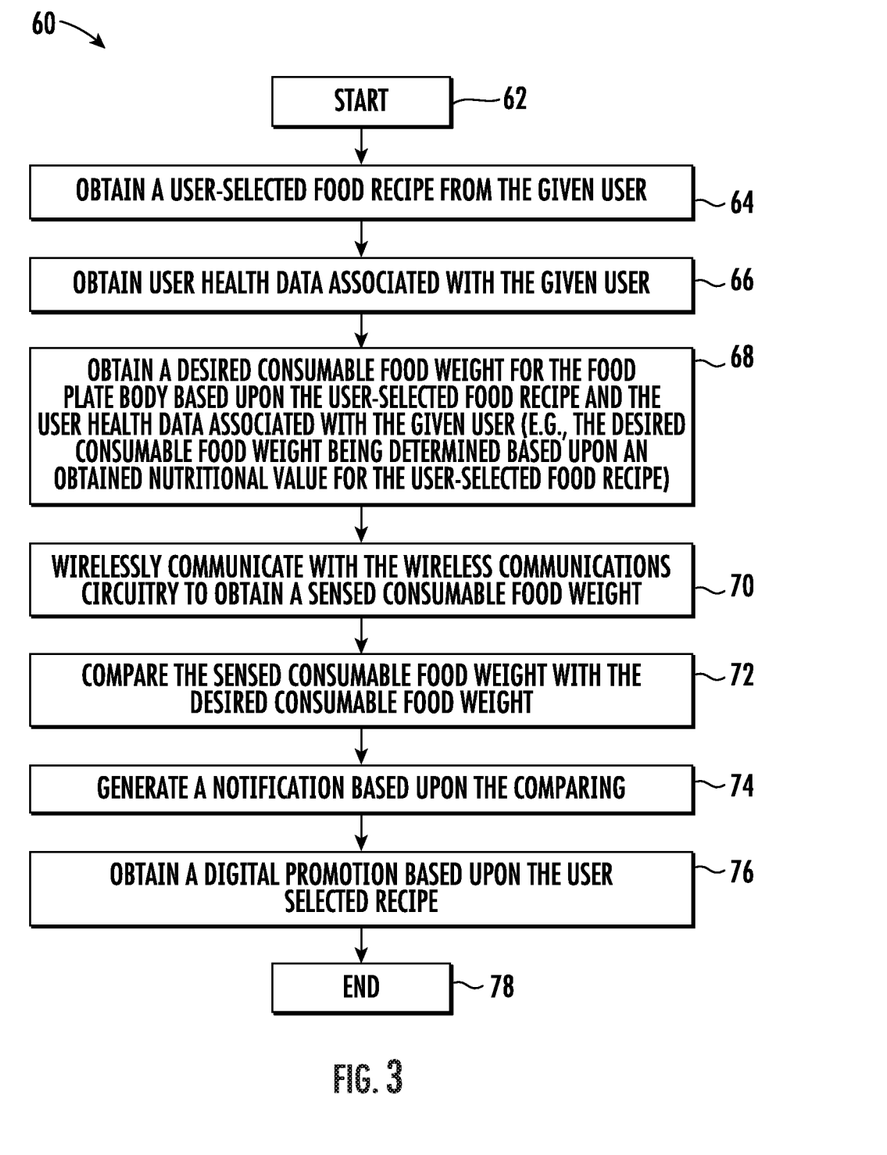
FIG. 3 is a flow diagram illustrating operation of the mobile wireless communications device of FIG. 2.

Referring now additionally to the flowchart 60 in FIG. 3, beginning at Block 62, operations of the mobile wireless communications device 40 with respect to food portioning will now be described. While operations of the mobile wireless communications device 40 are described herein, it should be understood that the operations are performed through cooperation between the mobile processor 42 and the memory 43.

At Block 64, the mobile wireless communications device 40 obtains a user-selected food recipe 24 from the given user, for example, by way of one of the input devices. The user-selected food recipe 24 may be selected from among food recipes associated with the given user. For example, the given user may select a food recipe from among food recipes that the given user has previously saved, liked (e.g., on social media), browsed (e.g., online via a browsing history), and/or purchased ingredients for (e.g., as part of a meal-kit as determined based upon a purchase history of the given user and accessed via a loyalty program identifier). The list of the food recipes may be generated or determined by the mobile wireless communications device 40. However, in some embodiments, a server, for example, a promotional sever 50, as will be described in further detail below, may determine the listing of food recipes and communicate the food recipe list to the mobile wireless communications device 40.

Each recipe may be defined by ingredients that form a food item. Each recipe may also be defined by one or more food items that make up a meal kit, for example.

The mobile wireless communications device 40, at Block 66, obtains user health data 23 associated with the given user. User health data 23 may include one or more of user weight data, user age data, user gender data, user fitness data, user nutritional goal data (e.g., diet data, such as if the given user is following a specific diet), and user biometric data (e.g., steps traveled, blood pressure, blood sugar, heartrate, etc.). The mobile wireless communications device 40 may obtain the health data 23 as input directly from the given user via the mobile wireless communications device (i.e., via an input device thereof). Alternatively or additionally, the mobile wireless communications device 40 may communicate (e.g., wirelessly) with a server and/or one or more peripheral devices (e.g., fitness trackers, fitness applications, etc.) to obtain the health data 23.

The mobile wireless communications device 40 obtains a desired consumable food weight 26 for the food plate body 31 based upon the user-selected food recipe 24 and the user health data 23 associated with the given user (Block 68). The desired consumable food weight 26 may be desired weight in terms of ounces, for example, that correspond to a desired caloric intake. For example, based upon the health data 23 (e.g., indicative that the given user is 10-pounds overweight), for the user-selected food recipe 24, the given user should have no more than 8-ounces of the selected food. The desired consumable food weight 26 may be determined based upon a look-up in a remote database or stored in the memory 43 of the mobile wireless communications device 40. The desired consumable food weight 26 may be determined based upon nutritional values and/or dietary guidelines (e.g., government provided, vitamin content, food content type, for example, protein, carbohydrate, etc.) or may be particular to a certain diet, and based upon fitness goals of the given user (e.g., a desire to lose 10-pounds). The fitness goals may be included as part of the health data 23, for example. The desired consumable food weight 26 may be obtained from the memory 43 of the mobile wireless communications device 40 or obtained from one or more remote servers, for example.

At Block 70 the mobile wireless communications device 40 wirelessly communicates, via the mobile device wireless communications circuitry 44, with the wireless communications circuitry 33 to obtain a sensed consumable food weight 25. The mobile wireless communications device 40 compares the sensed consumable food weight 25 with the desired consumable food weight 26 (Block 72), and generates a notification 28 based upon the comparing (Block 74). The notification 28 may be notification on the display 45 of the mobile wireless communications device 40, for example. The notification 28 may be in the form of a graphical icon that indicates whether there is too much food carried by or on the food plate body 31. For example, the sensed consumable food weight 25 may be displayed on the display 45 along with an icon (e.g., colored) or in a colored text that corresponds to whether the sensed consumable food weight exceeds the desired consumable food weight 26 (e.g., red). The notification 28 may alternatively or additionally include an email, short-message-service message, or other type of message. The notification 28 may also be communicated to another device or server. While a visual notification 28 has been described, the notification may be in the form of a haptic or tactile notification and/or audible notification.

At Block 76, the mobile wireless communications device 40 obtains a digital promotion 51 based upon the user-selected food recipe 24 from the promotional server 50. The digital promotion 51 may be displayed on the display 45 of the mobile wireless communications device 40, for example, or stored in a digital wallet associated with the given user.

More particularly, the promotional server 50 obtains the user-selected food recipe 24 from the mobile wireless communications device 40, for example, wirelessly, and generates the digital promotion 51 based upon the user-selected food recipe, and communicates, for example, wirelessly, the digital promotion to the mobile wireless communications device. The digital promotion 51 may be for another food recipe having one or more ingredients in common with the user-selected food recipe 24, for example. In some embodiments, the digital promotion 51 may be for another food recipe that has a higher nutritional value than the user-selected food recipe. For example, based upon the user health data 23 (e.g., fitness goals, health issues) which may be obtained by the promotional server 50, either directly from the given user or indirectly from the mobile wireless communications device 40, for example, the promotional server may determine a better recipe that would be furtherance, nutritionally, of the fitness goals or for addressing the given user's health issues (e.g., gluten free, fat free, sugar free, dairy free, etc.).

The digital promotion 51 has a promotional value associated therewith. The promotional server 50 may set the promotional value based upon the user health data 23. For example, the promotional value may be higher or increasing based upon the given user eating (e.g., as determined by the user-selected recipe 24 and the sensed consumable food weight 25) healthier foods or foods that support or are in furtherance of their fitness goals. Operations end at Block 78.

Figure 4:
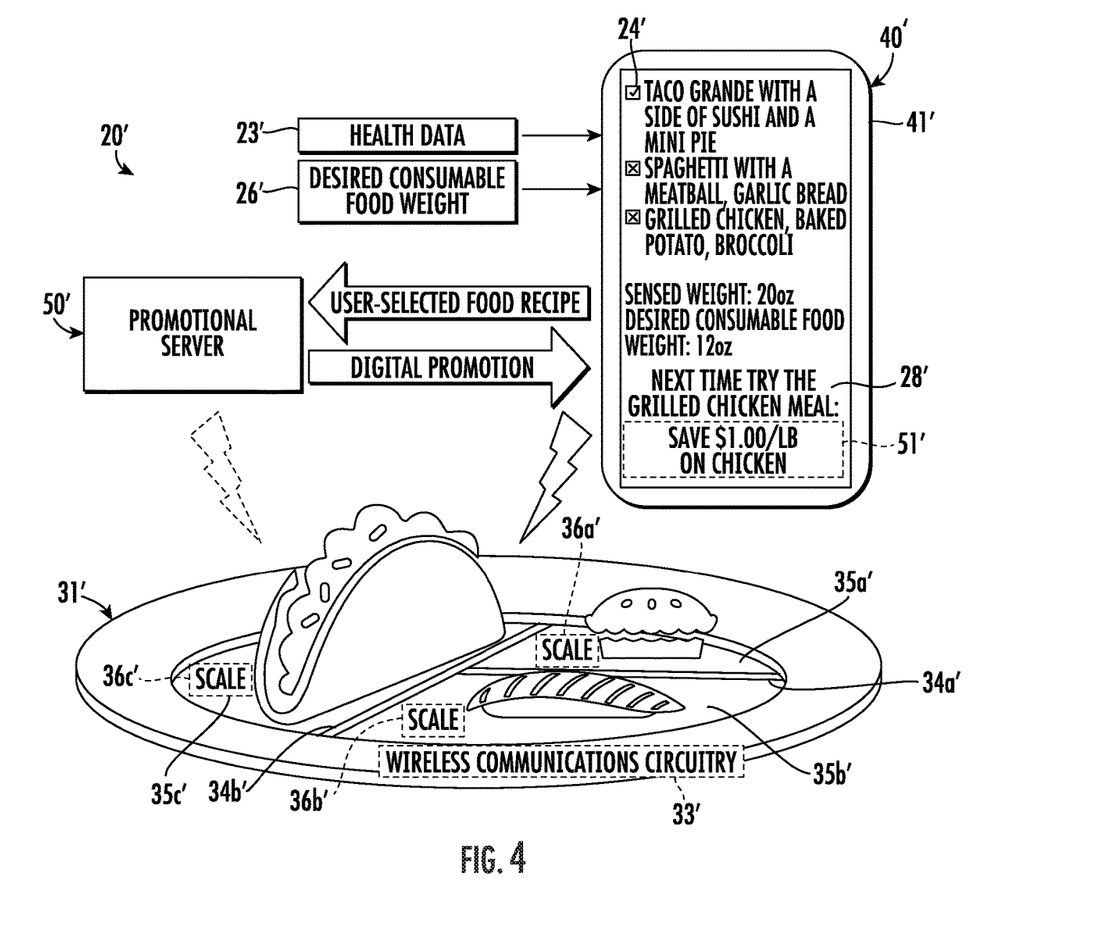
FIG. 4 is a schematic diagram of a food portioning system in accordance with another embodiment.

Referring now to FIG. 4, in another embodiment, the food plate body 31' includes partitions 34a', 34b' defining food compartments 35a'-35c'. Respective scales 36a'-36c' correspond to each respective food compartment 35a'-35c', for example, within the housing defined by the food plate body 31'. The scales 36a'-36c' sense the weight of the food carried by each food compartment 35a'-35c', individually (i.e., each scale senses a separate weight for the corresponding compartment independently from other compartments). Accordingly, the mobile wireless communications device 40' may obtain desired consumable food weights for each food or food recipe in each food compartment. This may be particularly advantageous when the given user is consuming multiple food recipes on a same plate or plate body 31' (e.g., vegetables, potato, meat). While there are two partitions 34a', 34b' illustrated, there may be any number of partitions, for example, one.

Figure 5:
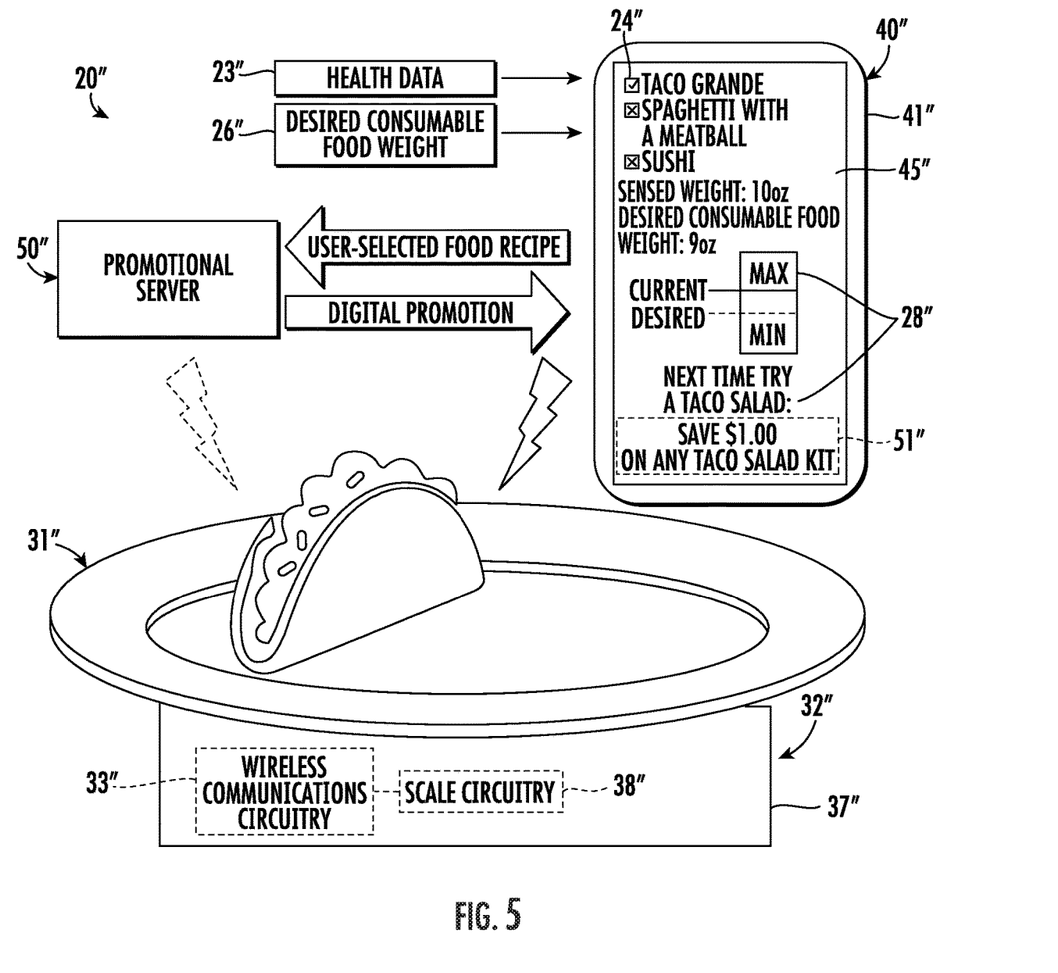
FIG. 5 is a schematic diagram of a food portioning system in accordance with another embodiment.

Referring now to FIG. 5, in another embodiment, the scale 32" is carrying the food plate body 31". More particularly, the scale 32" includes a scale housing 37" and scale circuitry 38" carried within the scale housing. The food plate body 31''', which may not define a housing, but rather may be a solid plate body, may be positioned on or carried by the scale housing 37" to obtain the weight of the food carried thereby. The wireless communications circuitry 33" may be carried by the scale housing 37".

A method aspect is directed to a method of portioning food in a food portioning system 20 that includes a food plate body 31, at least one scale 32 associated with the food plate body and configured to sense a weight of food carried thereby, and wireless communications circuitry 33 coupled to the at least one scale. The method includes using a mobile wireless communications device 40 to obtain a user-selected food recipe 24 from the given user, obtain user health data 23 associated with the given user, and obtain a desired consumable food weight 26 for the food plate body 31 based upon the user-selected food recipe and the user health data associated with the given user. The mobile wireless communications device 40 may also be used to wirelessly communicate with the wireless communications circuitry 33 to obtain a sensed consumable food weight 25, and compare the sensed consumable food weight with the desired consumable food weight 26, and generate a notification 28 based upon the comparing.

A computer readable medium aspect is directed to a non-transitory computer readable medium for portioning food in a food portioning system 20. The food partitioning system 20 includes a food plate body 31, at least one scale 32 associated with the food plate body and configured to sense a weight of food carried thereby, and wireless communications circuitry 33 coupled to the at least one scale. The non-transitory computer readable medium includes computer executable instructions that when executed by a processor 42 cause the processor to perform operations. The operations include obtaining a user-selected food recipe 24 from the given user, obtaining user health data 23 associated with the given user, and obtaining a desired consumable food weight 26 for the food plate body 31 based upon the user-selected food recipe and the user health data associated with the given user. The operations also include wirelessly communicating with the wireless communications circuitry 33 to obtain a sensed consumable food weight 25, and comparing the sensed consumable food weight with the desired consumable food weight 26, and generating a notification 28 based upon the comparing.

While several embodiments have been described herein, it should be appreciated by those skilled in the art that any element or elements from one or more embodiments may be used with any other element or elements from any other embodiment or embodiments. Many modifications and other That which is claimed is:

1. A food portioning system comprising:
a food plate body;
at least one scale associated with the food plate body and configured to sense a weight of food carried thereby;
wireless communications circuitry coupled to the at least one scale;
a mobile wireless communications device associated with a given user and configured to
obtain a user-selected food recipe from the given user,
obtain user health data associated with the given user,
obtain a desired consumable food weight for the food plate body based upon the user-selected food recipe and the user health data associated with the given user,
wirelessly communicate with the wireless communications circuitry to obtain a sensed consumable food weight, and
compare the sensed consumable food weight with the desired consumable food weight, and generate a notification based upon the comparing; and
a promotional server configured to
obtain the user-selected food recipe from the mobile wireless communications device,
generate a digital coupon redeemable toward another food recipe in response to obtaining the user-selected food recipe, the digital coupon being redeemable toward purchase of the another food recipe, and the another food recipe having a higher nutritional value than a nutritional value of the user-selected food recipe,
set a redeemable value of the digital coupon based upon the user health data, the sensed consumable food weight, and the nutritional value of the user-selected recipe so that the redeemable value increases relative to a higher nutritional value, and communicate the digital coupon to the mobile wireless communications device.

2. The food portioning system of claim 1 wherein the digital coupon is for another food recipe having at least one common ingredient with the user-selected food recipe.

3. The food portioning system of claim 1 wherein the mobile wireless communications device is configured to obtain the nutritional value for the user-selected food recipe, and determine the desired consumable food weight based upon the nutritional value.

4. The food portioning system of claim 1 wherein the user health data comprises at least one of user weight data, user age data, user gender data, user fitness data, user nutritional goal data, and user biometric data.

5. The food portioning system of claim 1 wherein the food plate body comprises at least one partition defining a plurality of food compartments; and wherein the at least one scale comprises a plurality of scales each corresponding to a respective food compartment.

6. The food portioning system of claim 1 wherein the at least one scale is coupled to the food plate body.

7. The food portioning system of claim 1 wherein the at least one scale is configured to carry the food plate body.

8. A food portioning system comprising:
at least one scale configured to sense a weight of food carried thereby;
wireless communications circuitry coupled to the at least one scale;
a mobile wireless communications device associated with a given user and configured to
obtain a user-selected food recipe from the given user,
obtain user health data associated with the given user,
obtain a desired consumable food weight based upon the user-selected food recipe and the user health data associated with the given user,
wirelessly communicate with the wireless communications circuitry to obtain a sensed consumable food weight, and
compare the sensed consumable food weight with the desired consumable food weight, and generate a notification based upon the comparing; and
a promotional server configured to
obtain the user-selected food recipe from the mobile wireless communications device,
generate a digital coupon redeemable toward another food recipe in response to obtaining the user-selected food recipe, the digital coupon being redeemable toward purchase of the another food recipe, and the another food recipe having a higher nutritional value than a nutritional value of the user-selected food recipe,
set a redeemable value of the digital coupon based upon the user health data, the sensed consumable food weight, and the nutritional value of the user-selected recipe so that the redeemable value increases relative to a higher nutritional value, and communicate the digital coupon to the mobile wireless communications device.

9. The food portioning system of claim 8 wherein the digital coupon is for another food recipe having at least one common ingredient with the user-selected food recipe.

10. The food portioning system of claim 8 wherein the mobile wireless communications device is configured to obtain the nutritional value for the user-selected food recipe, and determine the desired consumable food weight based upon the nutritional value.

* * * * *